United States Patent
Le

(10) Patent No.: US 11,865,152 B2
(45) Date of Patent: Jan. 9, 2024

(54) COMPOSITION OF NUTRITIONAL POWDER FROM GERMINATED DRAGON FRUIT SEEDS AND PROCESS OF MANUFACTURING THE SAME

(71) Applicant: Nguyen Ha Thi Le, Binh Thuan (VN)

(72) Inventor: Nguyen Ha Thi Le, Binh Thuan (VN)

(73) Assignee: PHUC HA JUICE CO., LTD, Binh Thuan (VN)

( * ) Notice: Subject to any disclaimer, the term of this patent is extended or adjusted under 35 U.S.C. 154(b) by 0 days.

(21) Appl. No.: 17/807,863

(22) Filed: Jun. 20, 2022

(65) Prior Publication Data

US 2023/0000938 A1 Jan. 5, 2023

(51) Int. Cl.
| | |
|---|---|
| *A61K 36/33* | (2006.01) |
| *A61K 36/746* | (2006.01) |
| *A23L 33/10* | (2016.01) |
| *A23L 19/00* | (2016.01) |

(52) U.S. Cl.
CPC .............. *A61K 36/33* (2013.01); *A23L 19/01* (2016.08); *A23L 33/10* (2016.08); *A61K 36/746* (2013.01); *A23V 2002/00* (2013.01); *A61K 2236/15* (2013.01); *A61K 2236/17* (2013.01); *A61K 2236/31* (2013.01)

(58) Field of Classification Search
CPC ............ A23V 2250/21; A23V 2200/30; A23V 2300/10; A23V 2300/38; A23L 2/60; A23L 2/52; A23L 33/10; A23L 33/00; A23L 19/00; A23L 33/105; A23L 2/44; A23L 19/01; A23L 2/39; A61K 36/33; A61K 2236/17

See application file for complete search history.

(56) References Cited

PUBLICATIONS

Du Y, Zhang Y and Zhou X, CN 106616348 A,, Machine English Translation, May 10, 2017 (Year: 2017).*

* cited by examiner

*Primary Examiner* — Hong T Yoo

(57) ABSTRACT

A composition of nutritional powder from germinated dragon fruit seeds was obtained from the process steps performed in the following specific order: (i) preparing materials, (ii) creating a dried germinated dragon fruit seeds mixture having moisture content lower than 10%, (iii) creating a foundation mixture, (iv) checking homogeneously of the foundation mixture, (v) determining whether adding the noni powder ingredient, (vi) creating a first temporary mixture, (vii) determining whether adding the dragon fruit powder ingredient, (viii) creating a second temporary mixture, (ix) determining whether adding the other ingredients, (x) creating a third temporary mixture, (xi) checking homogeneously of the third temporary mixture, (xii) grinding, and (xiii) adjusting humidity having less than 10%, then packing, and storing at room temperature. The composition of nutritional powder from germinated dragon fruit seeds is convenient for users to bring to eat/drink directly or to dilute with water and/or other food solutions when using.

12 Claims, 1 Drawing Sheet

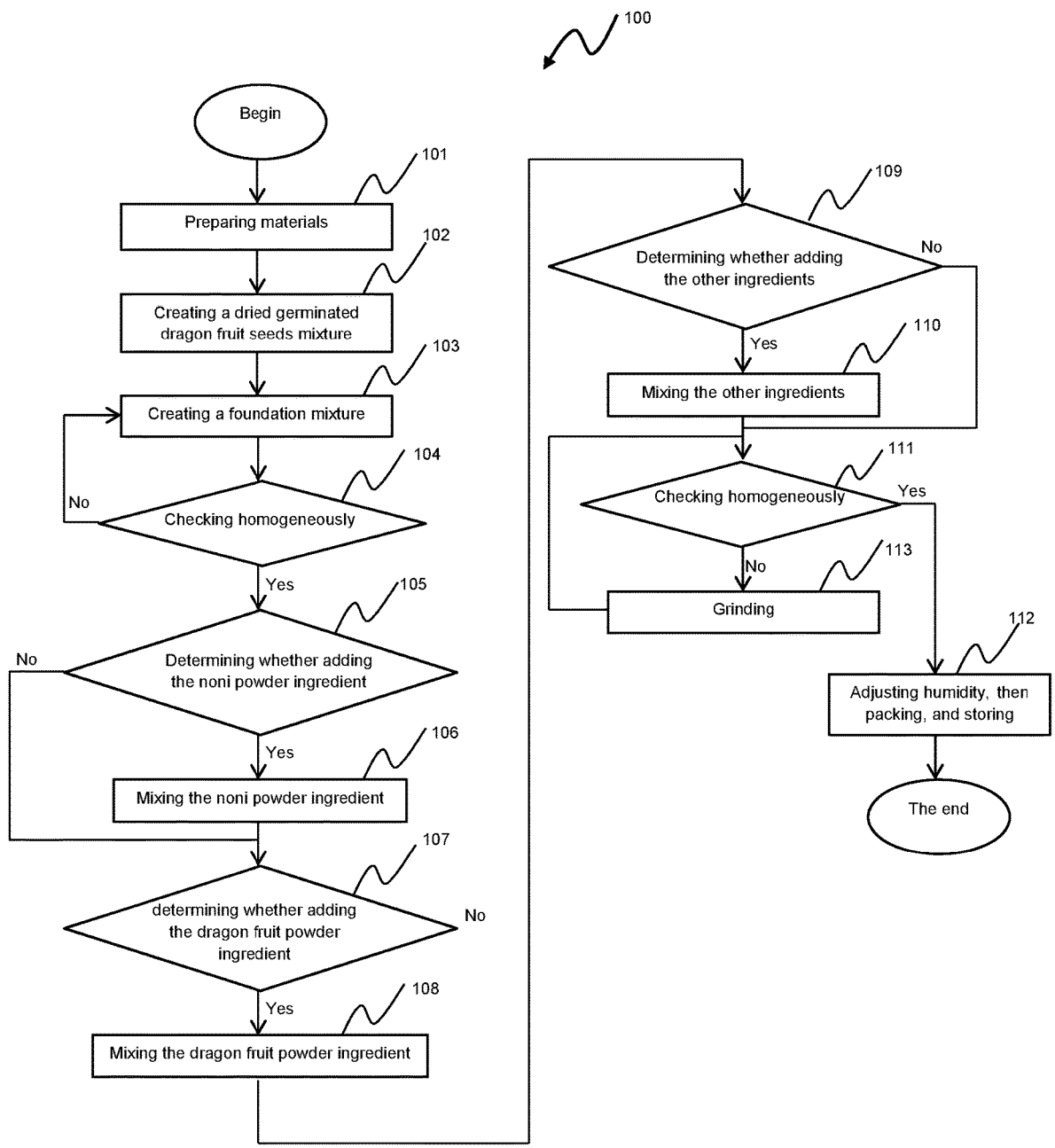

COMPOSITION OF NUTRITIONAL POWDER FROM GERMINATED DRAGON FRUIT SEEDS AND PROCESS OF MANUFACTURING THE SAME

FIELD OF THE INVENTION

The invention relates to the field of food processing technology. In particular, the present invention relates to a versatile food product that can be used not only as a beverage but also as a health-promoting functional food to improve immunity, skincare, and beauty for users. More specifically, the present invention relates to a composition of nutritional powder from germinated dragon fruit seeds and process of manufacturing the same.

BACKGROUND ART

Dragon fruit is classified in the group of 12 key fruit trees, also one of Vietnam's 9 specialty crops with competitive advantages in the world market. The area of dragon fruit growing in Vietnam is currently about 37,000 ha; wherein Binh Thuan province is considered Vietnam's dragon fruit "capital" with an area of up to 27,000 hectares, the annual output reaches more than 600,000 tons (accounting for 80% of the country's dragon fruit production). According to the Department of Industry and Trade, Binh Thuan' dragon fruit is consumed on the market mainly in the form of fresh dragon fruit and a few are processed products such as dragon fruit juice, dragon fruit wine, drying dragon fruit, freeze-drying dragon fruit, etc. However, due to the fact that fresh dragon fruit cannot be preserved for a long time, the consumption of dragon fruit is still the weakest stage, the domestic market only consumes about 15% of the output, and the remaining 85% is for export. Of these, the amount of fresh dragon fruit for official export accounts for a very low proportion (about 2-3%), the rest is consumed by cross-border trade with Chinese traders or sold to businesses outside the province which directly export. In order to stabilize the output of dragon fruit in line with the current rapidly increasing output, it is necessary to accelerate development, expand and diversify consumption markets both at home and abroad. That is one of the basic reasons for forming the idea of the process of manufacturing a composition of nutritional powder from germinated dragon fruit seeds, which contributes to increasing the economic value of dragon fruit.

According to actual data, despite the high nutritional content, dragon fruit seeds have not been fully utilized, specifically, dragon fruit seeds having 1.3%-1.5% by weight of the dragon fruit. Although, dragon fruit seeds account for a very low percentage compared to the flesh of the dragon fruit. The seeds have great nutritional value. Dragon fruit seeds contain many nutrients, which are important essential fatty acids such as linoleic acid (C18:2) and linolenic acid (C18:3) with concentrations ranging from 50% to 51%.

Several nutritional studies have explained the process of germinating seeds breaking down some starches, resulting in a higher nutrient ratio. It also breaks down phytate, a form of phytic acid that normally reduces the absorption of vitamins and minerals in the body. So, germinated seeds have more nutrients than regular grains. Research shows that sprouting reduces phytic acid content by up to 81%. Protease inhibitors were also reduced by 76%. This helps increase the absorption of proteins and important minerals for the body; such as iron, zinc, calcium, magnesium, and manganese. Besides, sprouted nuts are also low in starch; and easier to digest than regular grains.

According to patent application No. CN105011050, the present invention relates to preparation method of nutrient pitaya seed powder and products of nutrient pitaya seed powder. More specifically, the method comprises the following steps: 1) taking surplus pitaya seed and pulp residues after the preparation of fruit juice through homogenizing and filtering, adding 5-10 parts of water, adding pectinase and cellulase, and slowly stirring and treating the surplus pitaya seed, the pulp residues, the water, the pectinase and the cellulase for 12-72 hours; 2) performing filtration so as to obtain pitaya seed, and drying the obtained pitaya seed; 3) crushing the dried pitaya seed, and screening the crushed pitaya seed so as to obtain pitaya seed powder; and 4) disinfecting the pitaya seed powder, and subpackaging the disinfected pitaya seed powder so as to obtain finished products.

According to PH patent application PH22018000824, the present invention relates to a process of producing dragon fruit powder comprising the steps of: pureeing a predetermined quantity of peeled dragon fruit; mixing maltodextrin powder as a food additive with the puree; filtering the puree and maltodextrin powder mixture through a fine mesh filter to trap undissolved materials; pumping the mixture into a spray drying machine to convert the mixture in its liquid form to a powder; sieving the powder through a 40-mesh screen sifter; passing the powder through magnetic metal bars to trap metal contaminant; and packing a desired amount of the powder into a sealed container.

According to CN patent application No. CN104872566, the present invention relates to a health nutrition powder containing peanut, apricot kernels and dragon fruit, and a preparation method of the health nutrition powder. The health nutrition powder is prepared from the following raw materials in parts by weight: 25-30 parts of peanut powder, 20-25 parts of apricot kernel powder, 10-15 parts of dragon fruit powder, 10-15 parts of glutinous rice flour, 15-25 parts of traditional Chinese medicine powder and 5-8 parts of seasoning powder.

The above inventions meet the specific purposes and requirements of a technical solution. However, the disclosure of the main ingredients of nutritional powder from dragon fruit of all three inventions mentioned above does not disclose that the main ingredient is germinated dragon fruit seeds.

Therefore, it is necessary to create a composition of nutritional powder from germinated dragon fruit seeds that contains many good fatty acids for the body, such as omega-3 and omega-6 to help reduce the risk of cardiovascular disease, vitamin B3 has the effect of lowering harmful cholesterol (LDL) and increase good cholesterol (HDL).

Furthermore, it is necessary to provide a method of creating the composition of nutritional powder from germinated dragon fruit seeds having the addition of a noni powder to increase the nutritional, vitamin, and mineral values of the nutritional powder product from germinated dragon fruit seeds.

Finally, what is needed to provide a method of creating the composition of nutritional powder from germinated dragon fruit seeds includes simple steps, take advantage of the by-products of dragon fruit juice processing to diversify output products for dragon fruit, reduce waste to the environment and create a new source of raw materials "germinated dragon fruit seeds" for providing the production process.

This invention provides solutions to achieve the above goals.

SUMMARY OF THE INVENTION

Accordingly, an objective of the present invention is to provide a composition of nutritional powder from germinated dragon fruit seeds comprising a germinated dragon fruit seeds ingredient having a first percentage (%) by weight; a noni powder ingredient having a second percentage (%) by weight; a dragon fruit powder ingredient having a third percentage (%) by weight; and other ingredients having a fourth percentage (%) by weight; wherein the sum of said percentage (%) by weight of ingredients from the first percentage (%) to the fourth percentage (%) adds up to 100% by weight of said the composition of nutritional powder from germinated dragon fruit seeds.

Another objective of the present invention is to provide a method stimulating germinated fresh dragon fruit seeds or dried dragon fruit seeds using enzyme preparation including a cellulose enzyme ingredient and a pectin enzyme ingredient, having the effect of shortening the germination time. At the same time, the technical parameters of the germination process were investigated, which directly affect the nutritional composition of germinated dragon fruit seeds.

Another objective of the present invention is to provide a method of manufacturing the composition of nutritional powder from germinated dragon fruit seeds comprising the steps of: (i) preparing materials, (ii) creating a dried germinated dragon fruit seeds mixture having moisture content lower than 10%, (iii) creating a foundation mixture, (iv) checking homogeneously of the foundation mixture, (v) determining whether adding the noni powder ingredient, (vi) creating a first temporary mixture, (vii) determining whether adding the dragon fruit powder ingredient, (viii) creating a second temporary mixture, (ix) determining whether adding the other ingredients, (x) creating a third temporary mixture, (xi) checking homogeneously of the third temporary mixture, (xii) grinding, and (xiii) adjusting humidity having less than 10%, then packing, and storing at room temperature.

Yet another objective of the present invention is to provide a nutritional powder from germinated dragon fruit seeds has to prolong the time flavor-stabilizing properties, characteristic flavor, and nutritional ingredients depend on the percentage (%) by weight of each of the ingredients.

In view of the foregoing, another objective of the present invention is to provide a nutritional powder from germinated dragon fruit seeds using effectively the nutritional values of the noni powder. The nutrients in noni powder are combined with green foods of natural origin, which are germinated dragon fruit seeds, creating characteristic flavor and good for health.

Finally, the purpose of the invention is to provide a process of manufacturing the composition of nutritional powder from germinated dragon fruit seeds that is suitable for industrial production and does not pollute the environment.

These and other advantages of the present invention will no doubt become obvious to those of ordinary skill in the art after having read the following detailed description of the preferred embodiments, which are illustrated in the various drawing FIGURES.

BRIEF DESCRIPTION OF THE DRAWING

The accompanying drawings, which are incorporated in and form a part of this specification, illustrate embodiments of the invention and, together with the description, serve to explain the principles of the invention.

FIG. 1 is a flowchart illustrating a flowchart of a general method of manufacturing the composition of nutritional powder from germinated dragon fruit seeds in accordance with an exemplary embodiment of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

According to the embodiment of the present invention, a composition of nutritional powder from germinated dragon fruit seeds includes the ingredients listed in Table 1, including a germinated dragon fruit seeds ingredient having a first percentage (%) by weight; a noni powder ingredient having a second percentage (%) by weight; a dragon fruit powder ingredient having a third percentage (%) by weight; and other ingredients having a fourth percentage (%) by weight; wherein the sum of said percentage (%) by weight of ingredients from the first percentage (%) to the fourth percentage (%) adds up to 100% by weight of said the composition of nutritional powder from germinated dragon fruit seeds.

According to the embodiment of the present invention, the other ingredients including an additives ingredient, and a sweetener ingredient. The additives ingredient including a preservatives, and an anti-caking agents; wherein the anti-caking agents including calcium silicate, silicon dioxide, iron ammonium citrate, sodium aluminosilicate. The sweetener ingredient including a group of glucose, and a group of mixed natural sweeteners; wherein the group of glucose including monosaccharides, disaccharides; wherein the group of mixed natural sweeteners including invert sugar, hydrolyzed sugar from starch, honey, jaggery.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

According to the embodiment of the present invention, prolonged the time the flavor-stabilizing properties, characteristic flavor, and nutritional ingredients depend on the percentage (%) by weight of each of the ingredients listed in Table 1 including four formulas; wherein a third formula is more potent than a first formula, a fourth formula is more potent than a second formula; wherein the second formula is more potent than the first formula.

According to the preferred embodiment of the invention, the first formula comprises a germinated dragon fruit seeds ingredient having 20%-82% by weight, a noni powder ingredient having 0% by weight, a dragon fruit powder ingredient having 0% by weight, and other ingredients having 0%-20% by weight.

According to the preferred embodiment of the invention, the second formula comprises a germinated dragon fruit seeds ingredient having 20%-82% by weight, a noni powder ingredient having 0%-27% by weight, a dragon fruit powder ingredient having 0% by weight, and other ingredients having 0%-20% by weight.

According to the preferred embodiment of the invention, the third formula comprises a germinated dragon fruit seeds ingredient having 20%-82% by weight, a noni powder ingredient having 0% by weight, a dragon fruit powder ingredient having 0%-39% by weight, and other ingredients having 0%-20% by weight.

According to the preferred embodiment of the invention, the fourth formula comprises a germinated dragon fruit seeds ingredient having 20%-82% by weight, a noni powder ingredient having 0%-27% by weight, a dragon fruit powder ingredient having 0%-39% by weight, and other ingredients having 0%-20% by weight.

Now referring to FIG. 1, the method of manufacturing the composition of nutritional powder from germinated dragon fruit seeds 100 ("method 100") is based on the above principle in accordance with an exemplary embodiment of the present invention. In particular, method 100 includes from step 101 to step 113.

At step 101, preparing materials including a germinated dragon fruit seeds ingredient, a noni powder ingredient, a dragon fruit powder ingredient, and other ingredients. All ingredients are carefully selected and collected to ensure food safety and hygiene. Depending on the structural properties and chemical composition of each ingredient, the preparation method will be different.

According to the embodiment of the present invention, the germinated dragon fruit seeds ingredient obtained by a method stimulating germinated fresh dragon fruit seeds/dried dragon fruit seeds. The germinated dragon fruit seeds ingredient obtained by a method stimulating germinated fresh dragon fruit seeds or dried dragon fruit seeds including the steps of:
 (A) preparing materials including a dragon fruit seeds, and an enzyme preparation;
 the dragon fruit seeds is selected from the one or more of the following a white fleshed dragon fruit seeds with pink/red skin (*Hylocereus undatus*), a red flesh dragon fruit seeds with pink/red skin (*Hylocereus costaricensis/Hylocereus polyrhyzus*), a fleshy dragon fruit seeds white with yellow skin (*Hylocereus megalanthus*), a purple-pink flesh dragon fruit seeds with pink/red skin (*Hylocereus undatus costaricensis*); and the nutritional component of dragon fruit seeds is mentioned listed in Table 2;
 wherein the dragon fruit seeds further comprising a fresh dragon fruit seeds with a carbohydrate film surrounding dragon fruit seeds removed; a fresh dragon fruit seeds without removing a carbohydrate film surrounding dragon fruit seeds, a dried dragon fruit seeds having moisture content lower than 10%;
 wherein the enzyme preparation including a cellulose enzyme ingredient and a pectin enzyme ingredient; wherein a ratio of the cellulose enzyme ingredient and the pectin enzyme ingredient is selected one of the following ratios: 1:1, 1:2, 1:3, 2:1, 3:1 3:1, 4:1, and 5:1; preferably 2:1, 3:1 3:1, 4:1, and 5:1;
 (B) creating an enzyme solution by homogeneously mixing the enzyme preparation in step (A) with a water solvent in a ratio of (1-3) part the enzyme preparation: (1000-10000) part the water solvent;
 wherein the ratio of (1-3) part of the enzyme preparations and (5000-10000) part of the water solvent, which for soaking fresh dragon fruit seeds;
 wherein the ratio of 1 part of the enzyme preparations and (1000-5000) part the water solvent, which for soaking dried dragon fruit seeds;
 (C) creating an enzyme-treated dragon fruit seeds mixture by soaking the dragon fruit seeds in step (A) into the enzyme solution in step (B) in a ratio of 1 part the dragon fruit seeds to (3-7) part the enzyme solution at room temperature for 18-30 hours, preferably 24 hours;
 (D) creating a dragon fruit seed mixture before incubation by washing the enzyme-treated dragon fruit seeds mixture in step (C) with water, then spreading evenly on a cotton cloth, adjusting and maintaining a humidity of 70%-85% at room temperature;
 (E) incubating the dragon fruit seed mixture before incubation in step (C) in an anaerobic environment, at a temperature of 25° C.-32° C., humidity having 70%-85%, combined with spraying water 1-2 times/day;
 wherein the dragon fruit seed mixture before incubation is dried dragon fruit seeds having time incubation for 1-7 days;
 wherein the dragon fruit seed mixture before incubation is fresh dragon fruit seeds having time incubation for 12-60 hours.

It should be noted that the term "germinated dragon fruit seed" according to the invention includes the following meaning: germinated dragon fruit seeds are dragon fruit seeds with the most optimal value of protein, fat, and polyphenol nutritional components during incubation.

According to the embodiment of the present invention, all four formulations (first formula, second formula, third formula, and fourth formula) are listed in Table 1 for the composition of nutritional powder from germinated dragon fruit seeds having 20%-82% by weight of the germinated dragon fruit seeds ingredient.

Still with FIG. 1, continue to at step 102 creating a dried germinated dragon fruit seeds mixture having moisture content lower than 10% by drying the germinated dragon fruit seeds ingredient in step 102 at a temperature of 35° C.-50° C.

At step 103, creating a foundation mixture by grinding the dried germinated dragon fruit seeds mixture in step 102. Within the scope of the present invention, the term "foundation mixture" includes the following meanings:
 (a) A foundation mixture is a homogeneous mixture in size of germinated dragon fruit powder particles that have been grinding;
 (b) A foundation mixture is a mixture having humidified less than 10%; and
 (c) A foundation mixture act as a reactant, allowing the addition of ingredients including the noni powder ingredient, the dragon fruit powder ingredient, and the other ingredients the correct percentage (%) by weight, to contribute their chemical and physical properties to create a new preparation; this means that if there is no foundation mixture, the composition of nutritional powder from germinated dragon fruit seeds will not be formed.

At step 104, checking homogeneously of the foundation mixture in step 103 by using a sieve having a predetermined sieve hole size; if the foundation mixture passes through the predetermined sieve hole size, then performing step 105, otherwise repeat step 103. The term "homogeneous/homogeneously" is understood to mean the uniform distribution, or complete dissolution of, substances present in a solution/mixture.

At step 105, determining whether the noni powder ingredient is added to the foundation mixture in step 104; if the noni powder ingredient is added, then performing at step 106, otherwise performing at step 107.

At step 106, admixing the noni powder ingredient with the foundation mixture created a first temporary mixture. It should be noted that the term "admixed/mixed/admixing/mixing" as used in the present invention is understood to mean adding, or reacting, or dissolving homogeneously, or evenly, components in the same solution/mixture.

According to the embodiment of the present invention, the noni powder ingredient is selected from the one or more of the following a commercial noni powder, a noni powder obtained by a method drying and grinding the fresh/dried noni fruit. the noni powder obtained by a method drying and grinding the fresh/dried noni fruit including the steps of:

(A') preparing a noni fruit including a fresh noni fruit, a dried noni fruit;

wherein the dried noni fruit must be having a humidity content of less than 10%;

wherein the fresh noni fruit is selected according to the requirements of quality standards, chopped, cleaned, and dried to a humidity content of less than 10%;

(B') drying the noni fruit prepared in step (A') to a humidity content lower than 10%;

(C') grinding the dried noni fruit in step (B) obtained a noni powder ingredient.

According to the embodiment listed in Table 1, both formulations (first formula, and fourth formula) of the composition of nutritional powder from germinated dragon fruit seeds having 0% by weight of the noni powder ingredient. Both formulas (second formula, and third formula) of the composition of nutritional powder from germinated dragon fruit seeds having 0%-27% by weight of the noni powder ingredient.

At step 107, determining whether the dragon fruit powder ingredient is added to the first temporary mixture in step 106/the foundation mixture in step 104; if the dragon fruit powder ingredient is added, then performing at step 108, otherwise performing at step 109.

At step 108, admixing the dragon fruit powder ingredient with the first temporary mixture in step 106/the foundation mixture in step 104 created a second temporary mixture.

According to the embodiment of the present invention, the dragon fruit powder ingredient is selected from the one or more of the following a commercial dragon fruit powder, a dragon fruit powder obtained from dragon fruit pulp with the seeds removed, a dragon fruit powder obtained from dragon fruit pulp without removing dragon fruit seeds, a dragon fruit powder obtained from dragon fruit juice, a dragon fruit powder obtained from any part of the dragon fruit.

At step 109, determining whether the other ingredients are added to the second temporary mixture in step 108/the first temporary mixture in step 106/the foundation mixture in step 104; if the other ingredients are added, then performing at step 110, otherwise performing at step 111.

According to the embodiment listed in Table 1, both formulations (first formula, and second formula) of the composition of nutritional powder from germinated dragon fruit seeds have 0% by weight of the dragon fruit powder ingredient. Both formulations (third formula, and fourth formula) of the composition of nutritional powder from germinated dragon fruit seeds have 0%-39% by weight of the dragon fruit powder ingredient.

At step 110, admixing the other ingredients with the second temporary mixture in step 108/the first temporary mixture in step 106/the foundation mixture in step 104 created a third temporary mixture.

According to the embodiment of the present invention, the other ingredients including an additives ingredient, and a sweetener ingredient. The additives ingredient including a preservatives, and an anti-caking agents; wherein the anti-caking agents including calcium silicate, silicon dioxide, iron ammonium citrate, sodium aluminosilicate. The sweetener ingredient including a group of glucose, and a group of mixed natural sweeteners; wherein the group of glucose including monosaccharides, disaccharides; wherein the group of mixed natural sweeteners including invert sugar, hydrolyzed sugar from starch, honey, jaggery.

According to the embodiment of the present invention, all four formulations (first formula, second formula, third formula, and fourth formula) are listed in Table 1 for the composition of nutritional powder from germinated dragon fruit seeds having 0%-20% by weight of the other ingredients.

According to the preferred embodiment of the invention, the predetermined weight percentage (%) of the preservatives, the anti-caking agents, and the sweetener ingredient, are all listed in Table 3 below.

According to the embodiment of the present invention, steps 106, step 108, and step 110 are performed by a stirrer/mixer having a stirring speed of 200-400 rpm. The stirrer/mixer or other known apparatus of the same type has been known in previous art so the description of the structure and its operating principle will not be described in detail in the invention.

At step 111, checking homogeneously of the third temporary mixture in step 110 by using a sieve having a predetermined sieve hole size; if the third temporary mixture passes through the predetermined sieve hole size, then performing step 113, otherwise performing step 112. It is also noted that the sieve or other known apparatus of the same type has been known in previous art so the description of the structure and its operating principle will not be described in detail in the invention.

At step 112, grinding the third temporary mixture not passes through the predetermined sieve hole size in step 111; and then repeat step 111.

Finally, at step 113, adjusting humidity of the third temporary mixture passes through the predetermined sieve hole size in step 111 having less than 10%, then packing, and storing at room temperature.

The composition of nutritional powder from germinated dragon fruit seeds was obtained from the method 100 is convenient for users to bring to eat/drink directly or to dilute with water and/or other food solutions when using.

TABLE 1 components of the composition of nutritional powder from germinated dragon fruit seeds

| No. | Name of | Percentage (%) formulation | | | |
|---|---|---|---|---|---|
| | | First formula | Second formula | Third formula | Fourth formula |
| 1 | A germinated dragon fruit seeds ingredient | 20-82 | 20-82 | 20-82 | 20-82 |
| 2 | A noni powder ingredient | 0 | 0-27 | 0 | 0-27 |
| 3 | A dragon fruit powder ingredient | 0 | 0 | 0-39 | 0-39 |
| 4 | Other ingredients | 0-20 | 0-20 | 0-20 | 0-20 |

TABLE 2

Acid composition of dragon fruit seeds

| Chemical composition | Percentage (%) |
|---|---|
| Linoleic acid (C18:2) | 45-55 |
| Oleic Acid (C18:1) | 19-24 |
| Palmitic Acid (C16:0) | 15-18 |
| Stearic Acid (C18:0) | 7-8 |

TABLE 3

The other ingredients of the composition of nutritional powder from germinated dragon fruit seeds

| No. | Name of | Percentage (%) |
|---|---|---|
| 1 | Preservatives | 0.001-0.2 |
| 2 | Anti-caking agents | 0.001-0.2 |
| 3 | Sweetener ingredient | 0-20 |

According to the embodiment of the present invention, the production method produces 1 kg of the composition of nutritional powder from germinated dragon fruit seeds including four examples listed in Table 4 below.

TABLE 4

Mixed components of the composition of nutritional powder from germinated dragon fruit seeds in four examples according to the embodiment of the present invention.

| Examples | A germinated dragon fruit seeds (kg) | A noni powder (kg) | A dragon fruit powder (kg) | Sugar (kg) | Preservatives (kg) | Anti-caking agents (kg) |
|---|---|---|---|---|---|---|
| Example 1 | 30.5 | 20.5 | 38.5 | 10 | 0.2 | 0.3 |
| Example 2 | 50.5 | 0 | 35.5 | 13.5 | 0.2 | 0.3 |
| Example 3 | 60.5 | 21 | 0 | 18 | 0.2 | 0.3 |
| Example 4 | 81.5 | 0 | 0 | 18 | 0.2 | 0.3 |

According to the embodiment of the present invention, the composition of nutritional powder from germinated dragon fruit seeds obtained by method 100 has a humidity content of less than 10% and has a characteristic taste.

According to the embodiment of the present invention, the composition of method 100 takes advantage of the by-products of dragon fruit juice processing, increasing the diversity of output products from dragon fruit, creating raw materials for further processing, taking advantage of local labor resources, reducing the influence of seasonal factors, and minimizing the harmful effects of pollution on the environment. Integrating natural green raw materials is the germinated dragon fruit seeds with the noni powder and dragon fruit powder ingredients to create a composition of nutritional powder from germinated dragon fruit seeds with its own unique flavor; not only meet the nutritional and mineral needs of users but also contribute to building more images of Binh Thuan specialties in general and the two districts of Ham Thuan Bac and Ham Thuan Nam in particular. Besides, contribute to increasing the economic value of dragon fruit trees and participate in the OCOP project in Binh Thuan province.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes/comprises" and/or "including/comprising" when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A process of manufacturing a composition of nutritional powder from germinated dragon fruit seeds comprising steps performed in the following specific order:
   (i) preparing a germinated dragon fruit seeds ingredient having a first percentage (%) by weight by performing steps (A) to (E):
   (A) preparing a dragon fruit seeds, and an enzyme preparation;
      the dragon fruit seeds are selected from the one or more of the following a white dragon fruit seeds with pink or red skin (*Hylocereus undatus*), a red dragon fruit seeds with pink or red skin (*Hylocereus costaricensis* or *Hylocereus polyrhyzus*), a dragon fruit seeds white with yellow skin (*Hylocereus megalanthus*), a purple-pink dragon fruit seeds with pink or red skin (*Hylocereus undatus costaricensis*); wherein the dragon fruit seeds further comprising a dragon fruit seeds with a carbohydrate film surrounding dragon fruit seeds removed; a dragon fruit seeds without removing a carbohydrate film surrounding dragon fruit seeds, and a dried dragon fruit seeds having moisture content lower than 10%;
      the enzyme preparation including a cellulose enzyme ingredient and a pectin enzyme ingredient; wherein a ratio of the cellulose enzyme ingredient and the pectin enzyme ingredient is selected one of the following ratios: 1:1, 1:2, 1:3, 2:1, 3:1 3:1, 4:1, and 5:1;
   (B) creating an enzyme solution by homogeneously mixing the enzyme preparation in step (A) with a water in a ratio of (1-3) part the enzyme preparation: (1000-10000) part the water;
      wherein the ratio of (1-3) part of the enzyme preparations and (5000-10000) part of the water, which for soaking the dragon fruit seeds with the carbohydrate film surrounding dragon fruit seeds removed, and the dragon fruit seeds without removing the carbohydrate film surrounding dragon fruit seeds;
      wherein the ratio of 1 part of the enzyme preparations and (1000-5000) part the water, which for soaking the dried dragon fruit seeds having moisture content lower than 10%;
   (C) creating an enzyme-treated dragon fruit seeds mixture by soaking the dragon fruit seeds in step (A) into the enzyme solution in step (B) in a ratio of 1 part the dragon fruit seeds to (3-7) part the enzyme solution for 18-30 hours;
   (D) washing the enzyme-treated dragon fruit seeds mixture in step (C) with water, then spreading evenly on a cotton cloth, adjusting and maintaining a humidity of 70%-85%;
   (E) incubating said dragon fruit seed mixture in step (C) in an anaerobic environment, at a temperature of 25° C.-32° C., humidity having 70%-85%, combined with spraying water 1-2 times in one day, to create the germinated dragon fruit seeds ingredient;
   (ii) creating a dried germinated dragon fruit seeds mixture having moisture content lower than 10% by drying the germinated dragon fruit seeds ingredient in step (i) at a temperature of 35° C.-50° C.;
   (iii) creating a foundation mixture by grinding the dried germinated dragon fruit seeds mixture in step (ii);
   (iv) checking homogeneously of the foundation mixture in step iii) by using a sieve having a predetermined sieve hole size;
   if the foundation mixture passes through the predetermined sieve hole size, then performing step (v), otherwise repeat step (iii);
   (v) creating a first temporary mixture by mixing a noni powder ingredient having a second percentage (%) by weight with the foundation mixture; wherein the noni powder ingredient having moisture content of less than 10%;
   (vi) creating a second temporary mixture by mixing a dragon fruit powder ingredient having a third percentage (%) by weight with the first temporary mixture in step (v); wherein the dragon fruit powder ingredient is selected from the one in the following a powder of dragon fruit pulp with the seeds removed, and a powder of dragon fruit pulp without removing dragon fruit seeds;
   (vii) creating a third temporary mixture by mixing an other ingredients having a fourth percentage (%) by weight with the second temporary mixture in step (vi); wherein the other ingredients including an additives ingredient, and a sweetener ingredient;
   (viii) grinding and adjusting humidity the third temporary mixture having less than 10% to create the composition of nutritional powder from germinated dragon fruit seeds, then packing and storing.

2. The process of claim 1, wherein the additives ingredient including a preservatives, and an anti-caking agents;
   wherein the anti-caking agents including calcium silicate, silicon dioxide, iron ammonium citrate, and sodium aluminosilicate.

3. The process of claim 1, wherein the sweetener ingredient including a group of glucose, and a group of mixed natural sweeteners;
   wherein the group of glucose including monosaccharides, and disaccharides;
   wherein the group of mixed natural sweeteners including invert sugar, hydrolyzed sugar from starch, honey, and jaggery.

4. The process of claim 1, wherein at step (A) the ratio of the cellulose enzyme ingredient and the pectin enzyme ingredient is selected one of the following ratios: 2:1, 3:1 3:1, 4:1, and 5:1.

5. The process of claim 1, wherein at step (C) soaking the dragon fruit seeds in step (A) into the enzyme solution in step (B) in a ratio of 1 part the dragon fruit seeds to (3-7) part the enzyme solution for 24 hours.

6. The process of claim 1, wherein at step (E) time incubation is 1-7 days for the dried dragon fruit seeds having moisture content lower than 10%.

7. The process of claim 1, wherein at step (E) time incubation is 12-60 hours for the dragon fruit seeds with the carbohydrate film surrounding dragon fruit seeds removed, and the dragon fruit seeds without removing the carbohydrate film surrounding dragon fruit seeds.

8. The process of claim 1, wherein at step (i) the germinated dragon fruit seeds ingredient having 20%-82% by weight.

9. The process of claim 1, wherein at step (i) the noni powder ingredient having 27% by weight.

10. The process of claim 1, wherein at step (i) the dragon fruit powder ingredient having 39% by weight.

11. The process of claim 1, wherein at step (i) the other ingredients having 0.001%-20% by weight.

12. The process of claim 11, wherein the other ingredients containing the preservatives having 0.001%-0.2% by weight, and the anti-caking agents having 0,001%-0.2% by weight.

* * * * *